United States Patent
Krasnowski et al.

(10) Patent No.: US 10,408,723 B2
(45) Date of Patent: Sep. 10, 2019

(54) DISK BENDING SHEAR TESTING AND SYSTEM

(71) Applicant: Bell Helicopter Textron Inc., Fort Worth, TX (US)

(72) Inventors: Bogdan Roman Krasnowski, Bedford, TX (US); Xiaoming Li, Colleyville, TX (US); Chyau Tzeng, Arlington, TX (US); Robert Patrick Wardlaw, Keller, TX (US); Robert Arnold Brack, Bedford, TX (US)

(73) Assignee: BELL HELICOPTER TEXTRON INC., Fort Worth, TX (US)

( * ) Notice: Subject to any disclaimer, the term of this patent is extended or adjusted under 35 U.S.C. 154(b) by 156 days.

(21) Appl. No.: 15/379,808

(22) Filed: Dec. 15, 2016

(65) Prior Publication Data
US 2018/0172568 A1   Jun. 21, 2018

(51) Int. Cl.
*G01N 3/20* (2006.01)
*G01N 3/24* (2006.01)
(Continued)

(52) U.S. Cl.
CPC ............ *G01N 3/20* (2013.01); *G01N 3/02* (2013.01); *G01N 3/04* (2013.01); *G01N 3/24* (2013.01); *G01N 33/00* (2013.01); *G01N 2033/0003* (2013.01); *G01N 2203/001* (2013.01); *G01N 2203/0003* (2013.01); (Continued)

(58) Field of Classification Search
CPC .. G01N 3/20; G01N 3/04; G01N 3/02; G01N 3/24; G01N 33/00; G01N 2203/0266; G01N 2203/0062; G01N 2203/001; G01N 2203/0252; G01N 2203/0005; (Continued)

(56) References Cited

U.S. PATENT DOCUMENTS

| 8,656,788 B2 * | 2/2014 | Jeong | G01N 3/24 73/815 |
| 2013/0112013 A1 * | 5/2013 | Jeong | G01N 3/24 73/862.581 |

FOREIGN PATENT DOCUMENTS

EP          3336518 A1    6/2018
JP       H11304678 A     11/1999

OTHER PUBLICATIONS

Bao, et al. "Punch-shear tests and size effects for evaluating the shear strength of machinable ceramics" May 2004, Zeitschrift fur Metallkunde. 95, 372-376.
(Continued)

*Primary Examiner* — Jonathan M Dunlap
(74) *Attorney, Agent, or Firm* — Edwin S. Flores; Daniel J. Chalker; Chalker Flores, LLP (57) ABSTRACT

A method for determining a shear property of a sample includes supporting a sample at three or more separate support locations about a periphery of a first surface of the sample in a testing fixture, the sample including a second surface separated from the first surface by a thickness, wherein the sample is axisymmetric about an axis that is orthogonal to the first surface. The method includes applying a load on the second surface of the sample with a load applicator in a direction substantially parallel with the axis, measuring, with a controller, shear testing data of the sample in response to applying the load, and determining, with the controller, a shear property of the sample from the measured shear testing data.

36 Claims, 5 Drawing Sheets

(51) Int. Cl.
*G01N 3/02* (2006.01)
*G01N 3/04* (2006.01)
*G01N 33/00* (2006.01)

(52) U.S. Cl.
CPC ............... *G01N 2203/0005* (2013.01); *G01N 2203/0023* (2013.01); *G01N 2203/0062* (2013.01); *G01N 2203/0252* (2013.01); *G01N 2203/0266* (2013.01); *G01N 2203/0282* (2013.01)

(58) Field of Classification Search
CPC ... G01N 2203/0023; G01N 2203/0282; G01N 2033/003
USPC .... 73/849, 856, 812, 788, 159, 841; 702/42, 702/43, 34, 35, 33
See application file for complete search history.

(56) References Cited

OTHER PUBLICATIONS

Canadian Intellectual Property Office, Examination Report dated Dec. 27, 2017 for Canadian Application No. 2,957,879, 6 pp.
European Patent Office, European Search Report for EP Appl. No. 17155809.1 dated Oct. 19, 2017, 6 pp.
Bamford, et al. "Progressive Damage and Delamination in Composite Plates under Dynamic Loading: Analytical Modeling and Experimental Validation" Dec. 31, 2008, XP055405266, ISBN: 978-0-549-95840-6, https://search.proquest.com/docview/204640629.
Blackman, et al. "The determination of the mode II adhesive fracture resistance, G"I"I"C, of structural adhesive joints: an effective crack length approach" Engineering Fracture Mecha, Elsevier, Amsterdam, NL, vol. 72, No. 6, Dec. 18, 2004, pp. 877-897.
Lagunegrand, et al. "Design of an improved four point bending test on a sandwich beam for free edge delamination studies" Composites Part B: Engineering, Elsevier, UK, vol. 37, No. 2-3, Oct. 27, 2005, pp. 127-136, XP027846687, ISSN: 1359-8368, DOI: 10.1016/j.compositesb.2005.07.002.
Canadian Intellectual Property Office, Examination Report dated Oct. 15, 2018 for Canadian Application No. 2,957,879, 6 pp.
European Patent Office, Communication pursuant to Article 94(3) EPC for EP Appl. No. 17155809.1 dated Feb. 13, 2018, 6 pp.
European Patent Office, Communication pursuant to Article 94(3) EPC for EP Appl. No. 17155809.1 dated Sep. 19, 2018, 13 pp.

* cited by examiner

DISK BENDING SHEAR TESTING AND SYSTEM

STATEMENT REGARDING FEDERALLY SPONSORED RESEARCH OR DEVELOPMENT

This invention was made partially with government support under Army Technology Investment Agreement W911 W6-06-2-0002 awarded by National Rotorcraft Technology Center. The government has certain rights in the invention.

TECHNICAL FIELD

This disclosure relates to determining shear properties of a sample, for example, a composite laminate material.

BACKGROUND OF THE INVENTION

Composite structures, such as composite laminate structures, are used in a variety of industries. For example, the aircraft industry uses composite laminate structures for aircraft body panels, blades, and other elements. Composite laminate structures can experience structural defects in the form of delamination, voids, impact damage, marcels, ply wrinkles, and other defects during a lifetime of the composite laminate structure. A sample of a composite laminate structure can be tested to approximate shear characteristics of the composite laminate structure.

SUMMARY OF THE INVENTION

This disclosure describes methods and systems for disk bending shear testing samples, for example, laminate composite material samples.

In some aspects, a method for determining a shear property of a sample includes supporting a sample at three or more separate support locations about a periphery of a first surface of the sample in a testing fixture, the sample including a second surface separated from the first surface by a thickness. The method further includes applying a load on the second surface of the sample with a load applicator in a direction substantially orthogonal to the second surface of the sample, measuring shear testing data of the sample with a controller in response to applying the load, and determining a shear property of the sample from the measured shear testing data.

This, and other aspects, can include one or more of the following features. The three or more separate support locations can be equidistantly disposed about the periphery of the first surface. Supporting the sample at three or more separate support locations about a periphery of the first surface can include supporting the sample with three or more clamps at the three or more separate support locations about the periphery of the first surface. Supporting the sample at three or more separate support locations can include supporting the sample continuously about the entire periphery of the first surface. Supporting the sample continuously about the entire periphery of the first surface can include supporting the sample with a ring-shaped support structure about the periphery of the first surface. Determining a shear property of the sample from the measured shear testing data can include performing a data analysis on the shear testing data to determine the shear property. Determining a shear property of the sample from the shear testing data can include determining a shear stress of the sample. Applying a load on the second surface of the sample can include applying one of static loading, fatigue loading, or impact loading on the second surface of the sample. The sample can be rotationally symmetric about an axis that is orthogonal to the first surface. The sample can be axisymmetric about the axis. The load can be applied substantially along the axis. The sample may not be rotationally symmetric about the axis that is orthogonal to the first surface. The sample can have a surface profile of an irregular shape. The sample can include a laminate structure. The sample can include a composite laminate sample, wherein at least two laminate layers of the composite laminate sample are oriented in different directions. The method can include disposing, prior to applying the load on the second surface of the sample, at least one delamination insert between adjacent layers of the laminate structure to delaminate the adjacent layers of the laminate structure. The sample can include a bore hole in at least one of the first surface or the second surface of the sample. Applying a load on the second surface of the sample with a load applicator can include distributing the applied load over the second surface of the sample with a pad disposed between the sample and the load applicator. Determining a shear property of the sample from the shear testing data can include determining a stress state of the sample.

In some aspects of the disclosure, a system includes a support structure supporting a sample at three or more separate support locations about a periphery of a first surface of the sample, the sample including a second surface separated from the first surface by a thickness. The system includes a load applicator configured to apply a load on the second surface of the sample in a direction substantially orthogonal to the second surface of the sample, and a controller configured to control the load applied by the load applicator and measure shear testing data of the sample in response to the applied load.

This, and other aspects, can include one or more of the following features. The three or more separate support locations can be equidistantly disposed about the periphery of the first surface. The support structure can include three or more clamps positioned at the three or more separate support locations about the periphery of the first surface to support the sample. The support structure can include a ring-shaped support structure positioned about the periphery of the first surface of the sample, the ring-shaped support structure configured to support the sample continuously about the entire periphery of the first surface. The system can include a pad disposed between the sample and the load applicator to distribute the load applied on the second surface. The sample can include a bore hole in the first surface of the sample. The sample can include a composite laminate structure. The sample can include a composite laminate sample, wherein at least two laminate layers of the composite laminate sample are oriented in different directions. The sample can include at least one insert between adjacent layers of the laminate structure to delaminate the adjacent layers of the laminate structure. The sample can be rotationally symmetric about an axis that is orthogonal to the first surface. The sample can be axisymmetric about the axis. The sample may not be rotationally symmetric about the axis that is orthogonal to the first surface. The sample can have a surface profile of an irregular shape.

In some aspects of the disclosure, a method for determining shear properties of a sample includes supporting a sample continuously about an entire periphery of a first surface of the sample in a testing fixture, the sample including a second surface separated from the first surface by a thickness. The method includes applying a load on the second surface of the sample with a load applicator in a direction substantially orthogonal to the second surface, measuring, with a controller, shear testing data of the sample in response to applying the load, and determining shear properties of the sample from the shear testing data.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

For a more complete understanding of the features and advantages of the present invention, reference is now made to the detailed description of the invention along with the accompanying figures and in which.

Like reference numbers and designations in the various drawings indicate like elements.

DETAILED DESCRIPTION OF THE INVENTION

Illustrative embodiments of the system of the present application are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms such as "above," "below," "upper," "lower," or other like terms to describe a spatial relationship between various components or to describe the spatial orientation of aspects of such components should be understood to describe a relative relationship between the components or a spatial orientation of aspects of such components, respectively, as the device described herein may be oriented in any desired direction.

This disclosure describes a testing system for shear testing a sample, such as a composite laminate specimen, by supporting the sample in the testing system with distributed support about a periphery of the sample, and applying a load on a surface of the sample. The distributed support can include rotationally symmetric support, substantially even distribution of support (e.g., about a periphery of a sample), axisymmetric support (e.g., continuous support about an axis of the sample), and/or support otherwise disposed to distribute an applied load on a sample substantially evenly about the support. In some instances, the shape and/or surface profile of the sample is rotationally symmetric about an axis of the sample, such as a central axis of the sample. In this disclosure, rotational symmetry includes rotational symmetry to an order of two or three or more, up to an infinite order (e.g., axisymmetric symmetry, cylindrical symmetry). For example, a sample with a fifth order rotational symmetry can include a pentagon (e.g., pentagonal prism), an eighth order rotational symmetry can include an octagon (e.g., octagonal prism), and so on. The shape and/or surface profile of the sample can vary. In some instances, the sample can be axisymmetric, such as a cylindrical disk or other axisymmetric shape. In some examples, the sample can include an elliptical disk, or a disk with a surface profile of an irregular shape.

The testing system can be used to determine a shear property of a sample, such as interlaminar shear strength or shear stress of a composite laminate specimen. In some instances, when a composite laminate structure is loaded under bending, the structure experiences interlaminar shear stresses through a thickness of the composite laminate structure. Interlaminar shear strength can be determined, or at least approximated, by testing a sample in a testing system under loading, such as static, fatigue, and/or impact loading, measuring shear testing data of the sample, and determining shear properties (e.g., shear property data) of the sample.

Some conventional shear testing systems include a two-point-support, where a laminate (e.g., layered) test specimen is supported on two points, with a longitudinal axis spanning between the two support points. For example, some conventional shear testing systems test composite structures according to ASTM D2344 Short Beam Shear (SBS) testing, where a rectangular, unidirectional composite structure is tested under a two-point-support near each longitudinal end. This two-point-support can limit evaluation of the test specimen when exposed to a bending force, for example, such that shear property data is acquired only for a unidirectional laminar test specimen (e.g., layers oriented at zero degrees).

This disclosure describes an example testing system that supports (e.g., axisymmetrically supports) a laminate sample at three or more locations of the sample when exposed to an applied load, and measures shear testing data of the sample, for example, failure load, loading point displacement, and/or other, to determine a shear property or properties of the sample. The three or more support locations can be distributed evenly about the sample, and can include continuous support (e.g., axisymmetric support) about the sample. In some implementations, the layers of the laminate sample can be oriented at the same or different degrees along the thickness of the sample. In some examples of this disclosure, the testing system determines shear properties (e.g., interlaminar shear strength, shear stress, and/or other characteristic) of a composite sample that better exemplifies a composite element of a rotorcraft, aircraft, vehicle, windmill, turbine and/or other structure as compared to a testing system with a two-point-support, as described above. This is accomplished, for example, because the determined shear properties reflect shear characteristics of the sample in several (i.e., more than one) directions, instead of just a single direction (e.g., in a unidirectional rectangular sample). For example, the sample can include layers oriented in several (i.e., more than one) direction. In some examples, determined shear properties of a composite laminate sample that is supported in a testing system of this disclosure more closely represents shear properties of an actual composite structure (e.g., blade) of a rotorcraft, aircraft, vehicle, windmill, turbine, energy equipment, sports equipment, and/or other.

Figure 1:
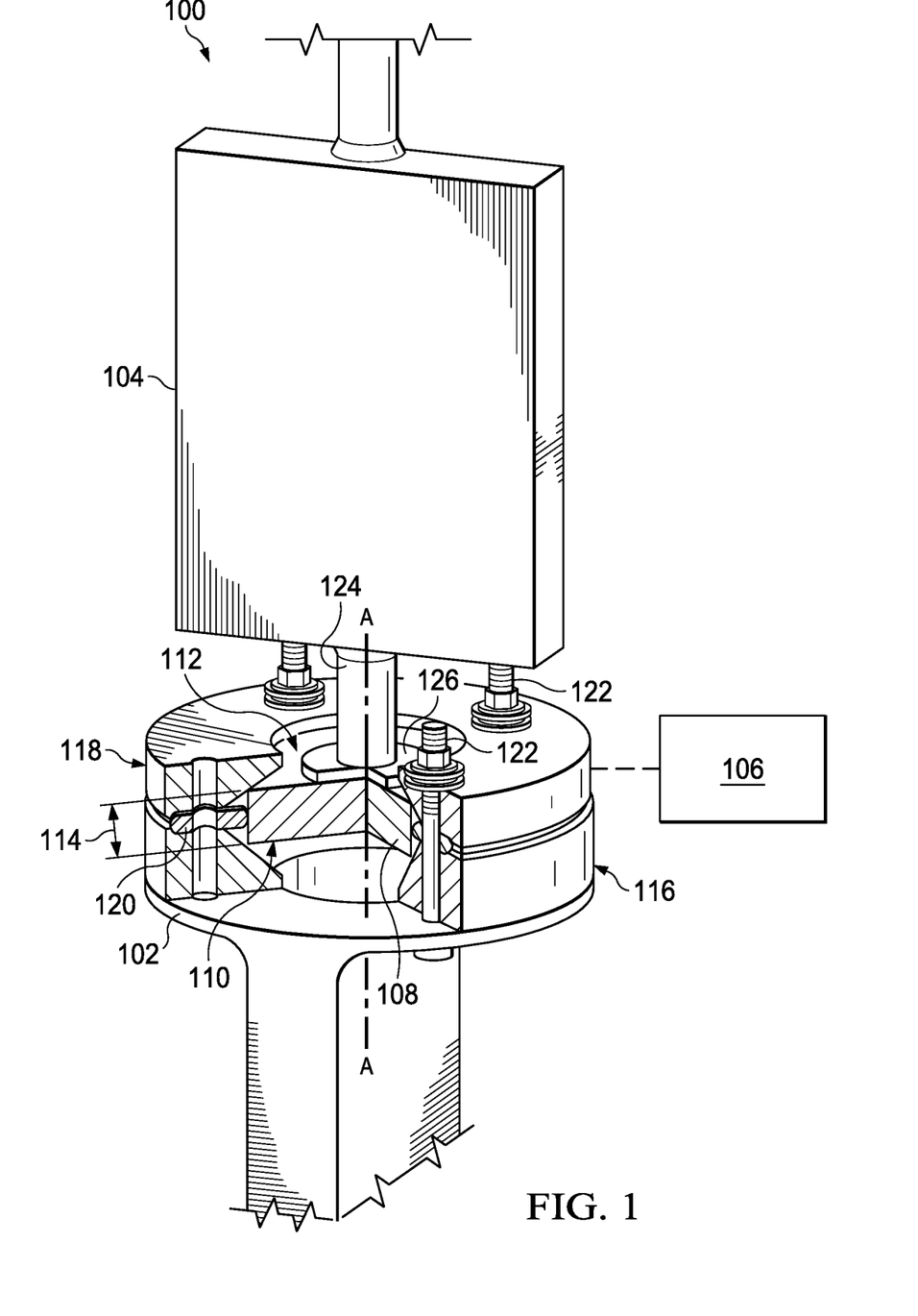
FIG. 1 is a partial schematic and partial cutaway perspective view of an example shear testing system.

FIG. 1 is a partial schematic perspective view of an example testing system 100. The testing system 100 includes a support structure 102 to support a sample 108, a load applicator 104 to apply a load on the sample 108, and a controller 106 to control the applied load and to measure shear testing data (e.g., failure load, loading displacement) of the sample 108. In some implementations, the controller and/or a data analysis of the shear testing data can determine a shear property or properties of the sample 108. The support structure 102 supports a sample 108 within the testing system 100 about a periphery of the sample 108, for example, by supporting a periphery of a first (e.g., bottom) surface of the sample 108. The sample 108 has a first surface 110, a second surface 112, and a thickness 114 separating the first surface 110 and the second surface 112. The first surface 110 is parallel to the second surface 112 in the example testing system 100 of FIG. 1; however, these surfaces can be oriented so that they are not parallel to each other. The example sample 108 is axisymmetric about an axis A-A that is orthogonal to the first surface 110. In the example system 100 of FIG. 1, the sample 108 defines a cylindrical disk, where the axis A-A is aligned with the centers of the first surface 110 and second surface 112. The sample 108 can take a variety of forms. For example, the sample 108 can be another shape, such as an elliptical disk, a rectangular block, or other rotationally symmetric shape, such as pentagonal, hexagonal, octagonal, or other multi-faceted shapes.

The example support structure 102 includes a first support member 116 and a second support member 118 substantially surrounding the sample 108 about the first surface 110 and second surface 112, respectively. In the example testing system 100 of FIG. 1, the first support member 116 and second support member 118 are substantially cylindrical with an opening in a center of each of the members 116 and 118. The first support member 116 includes a chamfered edge that engages the first surface 110 of the sample 108 about the periphery (e.g., outer edge) of the first surface 110. Similarly, the second support member 118 includes a chamfered edge that engages the second surface 112 of the sample 108 about the periphery (e.g., outer edge) of the second surface 112. A centering member 120 (e.g., centering ring) between the first support member 116 and second support member 118 and positioned about an outer arcuate surface of the sample 108 positions (e.g., centers) the sample 108 in the support structure 102. The centering member 120 is positioned in place with the first and second support members 116 and 118, and resides about the outer arcuate surface of the sample 108. The centering member 120 can include additional set screws, tabs, or other elements to position the sample 108 in the testing system 100.

In the example system 100 of FIG. 1, the first support member 116 supports the first surface 110 and the second support member 118 resides against the second surface 112 of the sample 108. In some implementations, the testing system 100 excludes the second support member 118 and/or the centering member 120, for example, such that the sample 108 sits atop the first support member 116 of the support structure 102. The first and second support members 116 and 118 are shown to be coupled by fasteners 122 (e.g., bolts). However, the first and second support members 116 and 118 can be connected in other ways. For example, the support members 116 and 118 can be coupled via slots.

In the example testing system 100 of FIG. 1, the load applicator 104 includes a plunger with a loading nose 124, for example, to engage and transmit a force to the second (e.g., top) surface 112 of the sample 108. The shape of the loading nose 124 can take a variety of forms. For example, the loading nose 124 can include a flat, rounded, pointed, multi-point, and/or other shaped end to engage the top surface 112 of the sample 108. The sample 108 is axisymmetric about an axis A-A that is orthogonal to its top surface 112. The load applicator 104, via the loading nose 124, applies a load on the top surface 112 of the sample 108 in a direction parallel to and/or aligned with the axis A-A, for example, such that a force applied to the sample 108 is perpendicular to the top surface 112 of the sample 108. In other instances, the load applicator 104 can apply a load on the top surface 112 of the sample 108 that is not parallel to the axis A-A. For example, the load applicator 104 can be set at an angled offset (e.g., between 0 and 90 degrees) from axis A-A. In some examples, the load applicator 104 and the loading nose 124 align with the axis A-A to apply the load on the top surface 112 of the sample 108 at the center of the top surface 112.

The load applicator 104 can apply a load on the sample 108 according to a specified testing procedure. For example, the load applicator 104 can apply static loading, fatigue loading, impact loading, and/or other loading on the sample 108. The controller 106 controls the type of loading applied on the sample 108, for example, in response to parameters set by an operator of the testing system, preset parameters, shear testing parameters for shear testing data intended to be measured, and/or other factors. The controller 106 measures shear testing data of the sample 108 (e.g., failure load and loading point displacement) in response to the applied load, and as such, shear properties (e.g., interlaminar shear strength, shear stress, and/or other) can be determined from the shear testing data. For example, a data analysis of the shear testing data can determine the shear properties of the sample 108.

In some implementations, such as that shown in FIG. 1, the testing system 100 includes a pad 126, such as a rubber, polymer, metal, and/or other material pad, positioned between the sample 108 and the loading nose 124 of the load applicator 104. The pad 126 distributes the applied load from the load applicator 104 across the second surface 112 of the sample 108, for example, better than load distribution of the loading nose 124 directly applied on the second surface 112. The pad 126 can be coupled to and/or integral to the loading nose 124, placed on the second surface 112 of the sample 108, adhered or otherwise connected to the second surface 112 of the sample 108, or otherwise disposed on the sample 108 to distribute the applied load. In the example testing system 100 of FIG. 1, the pad 126 includes a thin cylindrical disk with a diameter of about half of the sample diameter. However, the size, shape, and material of the pad can vary. For example, the pad 126 can extend over the entire second surface 112 of the sample 108, or extend over just a portion of the second surface 112 of the sample 108. In some examples, the pad 124 has an elliptical, rectangular, or other shape, and can be different from the shape of the second surface 112 of the sample 108.

In some instances, the shear properties determined from the shear testing data of the sample 108 tested in the example testing system 100 can be extrapolated to represent shear properties of a composite structure, for example, a composite blade, panel, or other element of a rotorcraft, aircraft, vehicle, windmill, turbine, energy equipment, sport equipment, and/or other. The support structure 102 supports the axisymmetric sample 108 such that an applied load on the second surface 112 provides data for shear properties of the sample 108 in more than one direction, for example, due in part to the multiple layers of the sample 108. The support structure can take a variety of forms to support the axisymmetric sample 108.

Figure 2:
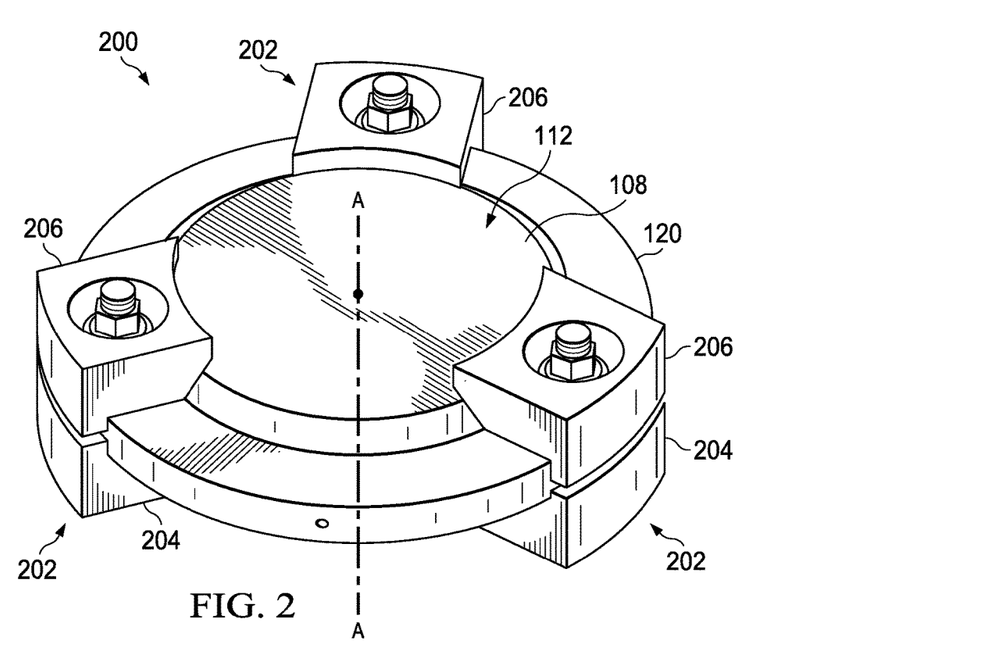
FIG. 2 is a quarter-sectional cutaway perspective view of an example support structure and sample for a shear testing system.
Figure 3:
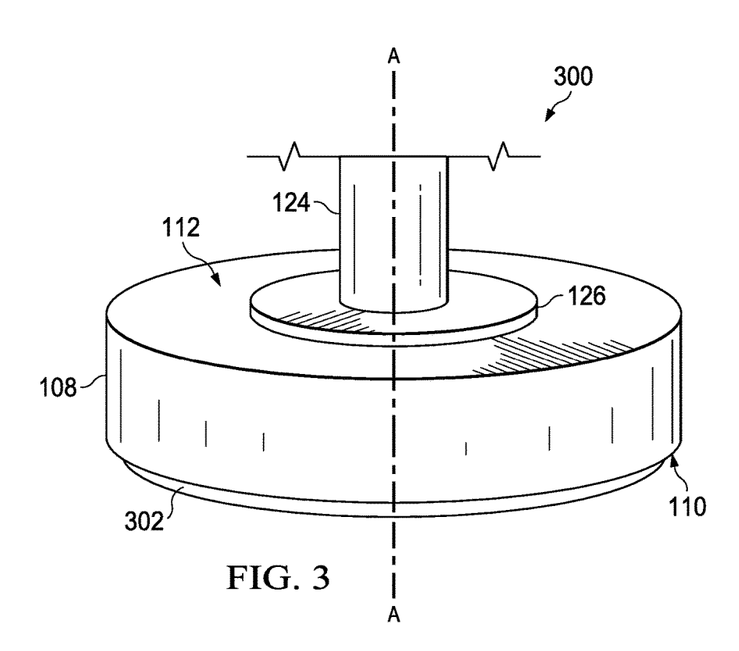
FIG. 3 is a quarter-sectional cutaway perspective view of an example support structure and sample for a shear testing system.

For example, FIGS. 2 and 3 are quarter-sectional cutaway perspective views of example point support structures 200 and 300, respectively, where each support structure 200 and 300 is shown supporting the example sample 108 of FIG. 1. The example support structures 200 and 300 can be used in the support structure 102 of FIG. 1.

Referring to FIG. 2, the example support structure 200 includes three clamps 202 disposed about the sample 108 to support the sample 108, for example, in the testing system 100 of FIG. 1. The support structure 200 also includes the centering member 120 of FIG. 1. In the example support structure 200 of FIG. 2, the clamps 202 are equidistantly disposed about the periphery of the sample 108. However, the number and location of the clamps 202 can vary. For example, the support structure 200 can include four or more clamps 202. The clamps 202 are spaced about the periphery of the sample 108 at separate locations, and can be evenly or unevenly distributed about the periphery of the sample 108. In some implementations, the clamps 202 are substantially or exactly evenly distributed about the periphery of the sample 108, for example, to provide axisymmetric support of the sample 108. In other implementations, the clamps 202 are not evenly distributed about the periphery of the sample 108. In certain examples, four or more clamps 202 are distributed about the periphery of the sample, where at least three of the four or more clamps 202 are evenly distributed about the periphery relative to each other (e.g., three clamps 202 disposed every 120 degrees about the circular periphery of the sample 108, additional clamps 202 disposed elsewhere).

Each clamp 202 includes a lower clamp member 204 and an upper clamp member 206 to support a portion of the first surface 110 (see FIG. 3) and a portion of the second surface 112, respectively, of the sample 108. The lower and upper clamp members 204 and 206 are contoured to support their respective surface of the sample 108. In the example support structure 200 of FIG. 2, the lower clamp member 204 includes a chamfered inner edge to engage a portion of the periphery of the first surface 110 of the sample 108. The upper clamp member 206 includes a chamfered inner edge to engage a portion of the periphery of the second surface 112 of the sample 108. In some instances, the contours can be different. For example, the lower and upper clamp members 204 and 206 can include a curved profile, an edge profile, a straight profile, and/or another profile to engage the sample 108.

Referring to FIG. 3, the example support structure 300 includes a support ring 302 positioned about the periphery of the first surface 110 of the sample 108 to continuously support the sample 108 about the entire periphery of the first surface 110. The support ring 302 defines a ring-shaped support structure, for example, that axisymmetrically supports the sample 108. Although FIG. 3 shows the support ring 302 as having a diameter slightly smaller than the diameter of the first surface 110 of the sample 108, the size of the support ring 302 can vary. For example, the diameter of the support ring 302 can vary to be substantially or exactly the same as the diameter of the sample 108. In some instances, the support ring 302 is shaped to substantially or exactly match a periphery of a sample, for example, when the sample is elliptical, rectangular, or irregularly shaped, or otherwise different than the circular disk shape of the sample 108 shown in FIG. 3. FIG. 3 also shows the loading nose 124 of the load applicator 104 of FIG. 1, and the optional pad 126 between the loading nose 124 and the sample 108.

Figure 4A:
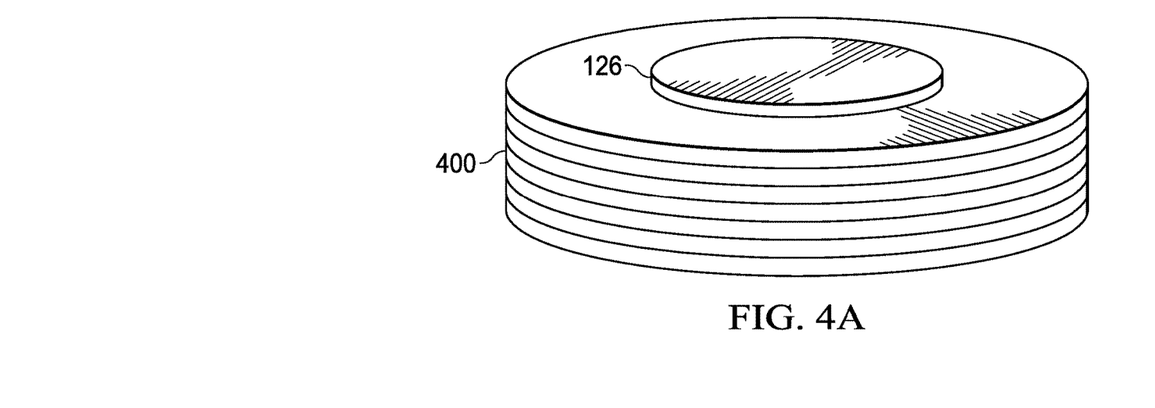
FIG. 4A is a side view of an example sample for a shear testing system.

The example sample 108 depicted in FIGS. 1-3 can take a variety of forms, for example, based on a desired shear test parameter. FIG. 4A is a side view of an example sample 400 with the pad 126 of FIG. 1. Example sample 400 can include a laminate structure including stacked layers (e.g., plies) of material, and can be used in the testing system 100 of FIG. 1 (e.g., as sample 108). The stacked layers can be oriented in the same or different directions throughout a thickness of the sample 400. FIGS. 4B-4F are partial cross-sectional cutaway views of example samples, such as the sample 400 of FIG. 1, with various modifications representing an interlaminar defect or failure that can be implemented on a sample. The samples of FIGS. 4B-4F can be used as the sample 108 in the testing system 100 of FIG. 1, for example, to determine a shear property of the respective sample under various failure conditions of the sample.

Figure 4B:
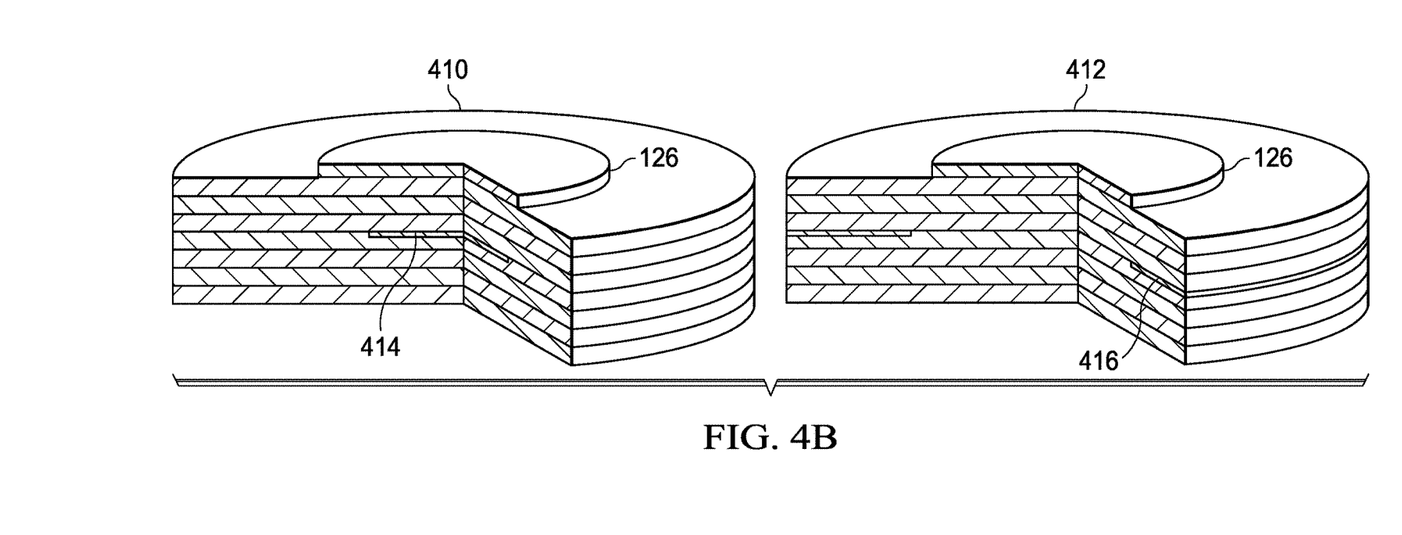
FIGS. 4B-4F are partial cross-sectional cutaway side views of example samples for a shear testing system.
Figure 4C:
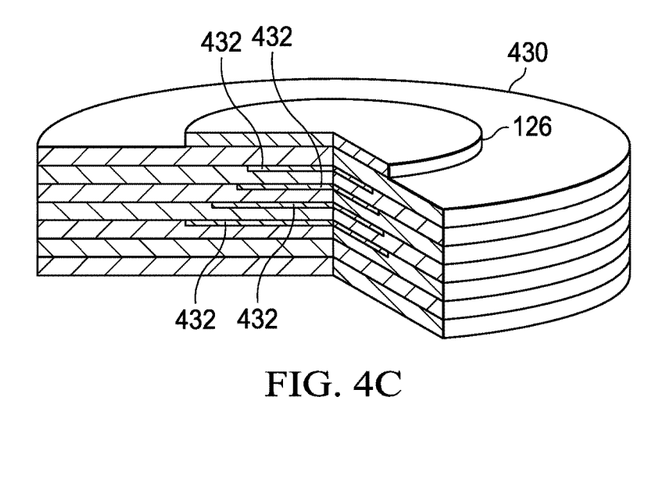
Figure 4D:
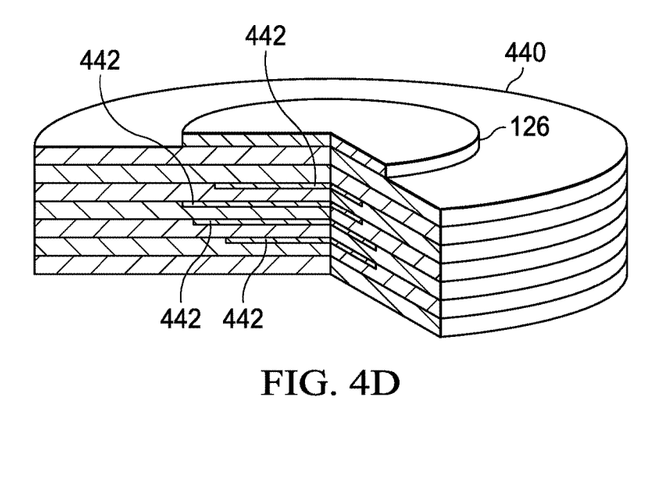
Figure 4E:
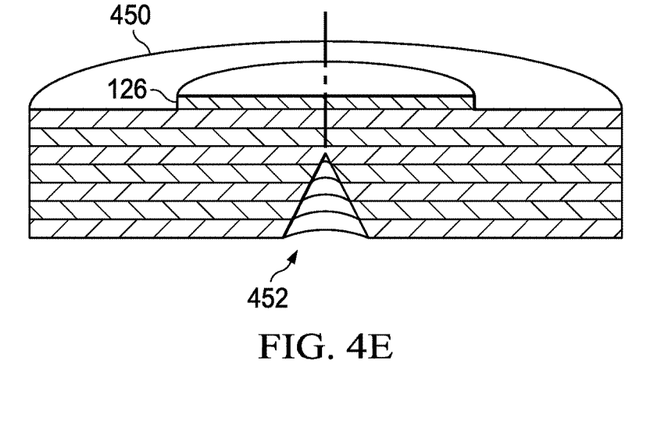
Figure 4F:
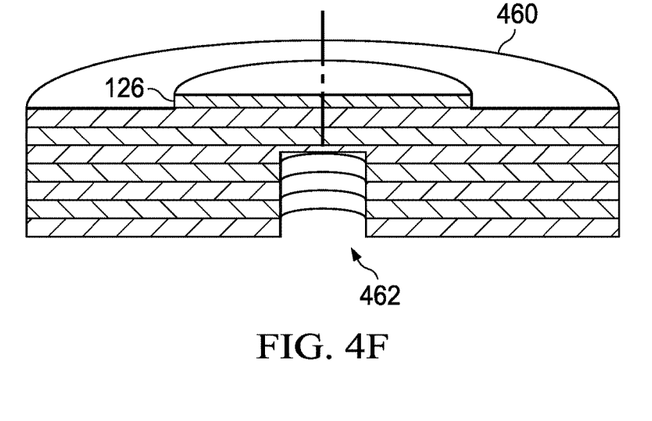

FIG. 4B shows a first sample 410 and a second sample 412, each sample 410 and 412 having a laminate composite structure. The first sample 410 includes a first insert 414 between two adjacent layers of the laminate composite structure at a radial center of the sample 410. The second sample 412 includes a second insert 416 between two adjacent layers of the laminate composite structure at a radially outer area of the sample 412. The first insert 414 and second insert 416 act to delaminate the adjacent layers of the laminate composite structure at the locations of the inserts 414 and 416, for example, to simulate a delamination of a sample during testing. The inserts 414 and 416 can include a variety of materials, for example, Teflon, and/or other materials. FIG. 4C shows a third sample 430, similar to the first sample 410 of FIG. 4B, except the third sample 430 includes multiple inserts 432 between multiple adjacent layers of the composite laminate structure. The third sample 430 with the multiple inserts 432 simulate, for example, an impact damage to the sample 430. FIG. 4D shows a fourth sample 440, similar to the third sample 430 of FIG. 4C, except the fourth sample 440 includes multiple inserts 442 within the sample 440 to simulate porosity or marcels (e.g., fiber waviness or wrinkles). FIG. 4E shows a fifth sample 450 with a cone-shaped hole 452 in a bottom surface of the sample 450. This cone-shaped hole 452 simulates, for example, a ply-drop in the sample 450. FIG. 4F shows a sixth sample 460 with a cylindrical bore hole 462 in a bottom surface of the sample 460. This cylindrical bore hole 462 simulates, for example, wrinkles in the layered plies of the composite structure of the sample 460.

Figure 5:
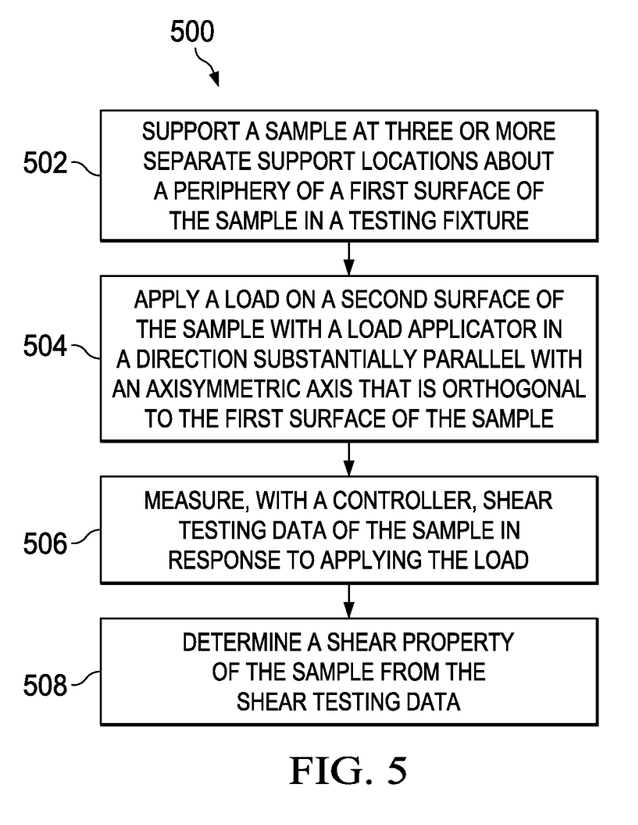
FIG. 5 is an example flowchart for determining a shear property of a sample.

FIG. 5 is a flow chart describing an example method 500 for determining a shear property of a sample, for example, performed by the example testing system 100 of FIG. 1. At 502, a sample is supported at three or more separate support locations about a periphery of a first surface of the sample in a testing fixture. The sample includes a second surface separated from the first surface by a thickness. The sample is axisymmetric about an axis that is orthogonal to the first surface. The sample can include the example sample 108 of FIGS. 1-3, example sample 400 of FIG. 4A, first sample 410 of FIG. 4B, second sample 412 of FIG. 4B, third sample 430 of FIG. 4C, fourth sample 440 of FIG. 4D, fifth sample 450 of FIG. 4E, sixth sample 460 of FIG. 4F, or another sample. At 504, a load is applied on the second surface of the sample with a load applicator in a direction substantially parallel with (e.g., aligning with) the axis. In some implementations, a controller controls the load applicator to apply the load according to shear parameters, characteristics of the sample, test type (e.g., static, fatigue, or impact loading), and/or or other factors. At 506, shear testing data of the sample is measured with a controller in response to applying the load. At 508, a shear property of the sample is determined from the measured shear testing data, for example, from a data analysis of the shear testing data performed at least in part by the controller.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the devices and/or methods disclosed and claimed herein can be made and executed without undue experimentation in light of the present disclosure. While the devices and/or and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

Furthermore, no limitations are intended to the details of construction or design herein shown, other than as described in the claims below. It is therefore evident that the particular embodiments disclosed above may be altered or modified and all such variations are considered within the scope and spirit of the disclosure. Accordingly, the protection sought herein is as set forth in the claims below.

To aid the Patent Office, and any readers of any patent issued on this application in interpreting the claims appended hereto, applicants wish to note that they do not intend any of the appended claims to invoke paragraph 6 of 35 U.S.C. § 112 as it exists on the date of filing hereof unless the words "means for" or "step for" are explicitly used in the particular claim.

What is claimed is:

1. A method for determining a shear property of a sample, the method comprising:
  supporting a sample at three or more support locations about a periphery of a first surface of the sample in a testing fixture without any penetration of the sample, the sample is axisymmetric about an axis that is orthogonal to the first surface and comprises a second surface separated from the first surface by a thickness;
  applying a load on the second surface of the sample with a load applicator in a direction substantially orthogonal to the second surface of the sample;
  measuring, with a controller, shear testing data of the sample in response to applying the load, wherein the shear testing data comprises the applied load and a loading point displacement; and determining, with the controller, a shear property of the sample from the measured shear testing data, wherein the shear property comprises a laminar shear strength or a shear stress.

2. The method of claim 1, wherein the three or more support locations are equidistantly disposed about the periphery of the first surface.

3. The method of claim 1, wherein supporting the sample at three or more support locations about the periphery of the first surface comprises supporting the sample with three or more clamps, each clamp comprising a lower clamp member having a first chamfered surface at the three or more support locations about the periphery of the first surface, and an upper clamp member having a second chamfered surface.

4. The method of claim 1, wherein supporting the sample at three or more support locations comprises a first support member having a first chamfered surface supporting the sample continuously about the entire periphery of the first surface, and a second support member having a second chamfered surface.

5. The method of claim 4, wherein supporting the sample continuously about the entire periphery of the first surface comprises supporting the sample with a ring-shaped support structure having a first chamfered surface about the periphery of the first surface.

6. The method of claim 1, wherein determining the shear property of the sample from the measured shear testing data comprises performing a data analysis on the shear testing data to determine the shear property.

7. The method of claim 1, wherein determining the shear property of the sample from the shear testing data comprises determining a shear stress of the sample.

8. The method of claim 1, wherein applying the load on the second surface of the sample comprises applying one of static loading, fatigue loading, or impact loading on the second surface of the sample.

9. The method of claim 1, wherein the sample is rotationally symmetric about the axis.

10. The method of claim 9, wherein the sample comprises an axisymmetrical disk.

11. The method of claim 9, wherein the load is applied substantially along the axis.

12. The method of claim 1, wherein the sample is not rotationally symmetric about the axis.

13. The method of claim 1, wherein the sample comprises a surface profile of an irregular shape.

14. The method of claim 1, wherein the sample comprises a laminate structure.

15. The method of claim 14, wherein the sample comprises a composite laminate sample, wherein at least two laminate layers of the composite laminate sample are oriented in different directions.

16. The method of claim 14, comprising disposing, prior to applying the load on the second surface of the sample, at least one delamination insert between adjacent layers of the laminate structure to delaminate the adjacent layers of the laminate structure.

17. The method of claim 1, comprising including, prior to applying the load on the second surface of the sample, a cone-shaped hole or a cylindrical bore hole aligned with the axis in at least one of the first surface or the second surface of the sample.

18. The method of claim 1, wherein applying the load on the second surface of the sample with the load applicator comprises distributing the applied load over the second surface of the sample with a pad disposed between the sample and the load applicator.

19. The method of claim 1, wherein determining the shear property of the sample from the shear testing data comprises determining a stress state of the sample.

20. The method of claim 1, further comprising centering the sample using a centering member.

21. A system, comprising:
a support structure supporting a sample at three or more support locations about a periphery of a first surface of the sample without any penetration of the sample, the sample is axisymmetric about an axis that is orthogonal to the first surface and comprises a second surface separated from the first surface by a thickness;
a load applicator configured to apply a load on the second surface of the sample in a direction substantially orthogonal to the second surface of the sample; and
a controller configured to control the load applied by the load applicator and measure shear testing data of the sample in response to the applied load, wherein the shear testing data comprises the applied load and a loading point displacement.

22. The system of claim 21, wherein the three or more support locations are equidistantly disposed about the periphery of the first surface.

23. The system of claim 21, wherein the support structure comprises three or more clamps, each clamp comprising a lower clamp member having a first chamfered surface positioned at the three or more support locations about the periphery of the first surface to support the sample, and an upper clamp member having a second chamfered surface.

24. The system of claim 21, wherein the support structure comprises a ring-shaped support structure having a first chamfered surface positioned about the periphery of the first surface of the sample, the ring-shaped support structure configured to support the sample continuously about the entire periphery of the first surface.

25. The system of claim 21, further comprising a pad disposed between the sample and the load applicator to distribute the load applied on the second surface.

26. The system of claim 21, wherein the sample comprises a cone-shaped hole or a cylindrical bore hole aligned with the axis in the first surface of the sample.

27. The system of claim 21, wherein the sample comprises a composite laminate structure.

28. The system of claim 27, wherein the sample comprises a composite laminate sample, wherein at least two laminate layers of the composite laminate sample are oriented in different directions.

29. The system of claim 27, wherein the sample comprises at least one insert between adjacent layers of the laminate structure to delaminate the adjacent layers of the laminate structure.

30. The system of claim 21, wherein the sample is rotationally symmetric about the axis.

31. The system of claim 30, wherein the sample comprises an axisymmetrical disk.

32. The system of claim 21, wherein the sample is not rotationally symmetric about the axis.

33. The system of claim 21, wherein the sample comprises a surface profile of an irregular shape.

34. The system of claim 21, wherein the support structure further comprises a centering member positioned about an outer surface of the sample.

35. A method for determining shear properties of a sample, the method comprising:
supporting a sample continuously about an entire periphery of a first surface of the sample in a testing fixture without any penetration of the sample, the sample is axisymmetric about an axis that is orthogonal to the first surface and comprises a second surface separated from the first surface by a thickness, and the testing fixture comprises a first support member having a first chamfered surface supporting the sample continuously about the entire periphery of the first surface, and a second support member having a second chamfered surface engaging the second surface of the sample;

applying a load on the second surface of the sample with a load applicator in a direction substantially orthogonal to the second surface;

measuring, with a controller, shear testing data of the sample in response to applying the load, wherein the shear testing data comprises the applied load and a loading point displacement; and determining, with the controller, shear properties of the sample from the shear testing data, wherein the shear property comprises a laminar shear strength or a shear stress.

36. The method of claim 35, wherein the testing fixture further comprises a centering member between first support member and the second support member.

* * * * *